United States Patent [19]

Robbins

[11] Patent Number: 4,625,574

[45] Date of Patent: Dec. 2, 1986

[54] LIQUID SAMPLING METHOD AND MEANS

[76] Inventor: Robert J. Robbins, Rte. 2, Box 6, Lodi, Wis. 53555

[21] Appl. No.: 769,136

[22] Filed: Aug. 26, 1985

[51] Int. Cl.⁴ ............................................. G01N 1/10
[52] U.S. Cl. ............................... 73/864.63; 73/864.91
[58] Field of Search ........... 73/864.63, 864.91, 864.86, 73/864.65, 864.66, 863.23

[56] References Cited

U.S. PATENT DOCUMENTS

| | | | |
|---|---|---|---|
| 1,585,072 | 5/1926 | Banks | 73/864.63 |
| 3,714,830 | 2/1973 | Keir | 73/864.63 |
| 4,004,463 | 1/1977 | Puthoff et al. | 73/864.66 |
| 4,215,580 | 8/1980 | Barsaloux | 73/864.66 |
| 4,346,612 | 8/1982 | Rand | 73/864.63 |

Primary Examiner—Stewart J. Levy
Assistant Examiner—Robert R. Raevis
Attorney, Agent, or Firm—Keith Schoff

[57] ABSTRACT

Method and apparatus are disclosed for obtaining a field sample from a body of liquid which preserves sample quality against deterioration resulting from contamination, aeration, or escape of volatile components. The procedure involves fitting the field sampling container with septum cap and sealed end closures after the sample is taken and using the container for transport and storage of the sample prior to analysis.

5 Claims, 2 Drawing Figures

LIQUID SAMPLING METHOD AND MEANS

BACKGROUND OF THE INVENTION

Field sampling of liquids contained in wells, barrels, surface or subsurface reservoirs, storage tanks and the like is commonly accomplished by immersing an empty vessel in the liquid, withdrawing it when full, and transferring the contents from the vessel to a transport container by pouring the contents from one to the other. At a later time the transport vessel is opened at a laboratory and the sample is analysed. The procedure serves satisfactorily for determining components present in gross amounts, but is unsatisfactory for measuring minute quantities of components, or for obtaining an accurate analysis of components which can be altered or lost due to aeration or volatilization. It is particularly important to utilize appropriate procedure and means for obtaining accurate analysis when testing for trace amounts of environmental pollutants, e.g. hydrocarbons, pesticides or heavy metals in water samples, and for avoiding sample contamination.

SUMMARY OF THE INVENTION

A sampling procedure and device are disclosed in which the sampling vessel is fitted with septum cap and closures to serve as transport and storage vessel for a sample prior to analysis thereby to eliminate the possibility of cross-contamination occurring by carry-over of residue from a previously contained material in a transport vessel to a fresh sample, and to eliminate aeration of a sample resulting from pouring the sample liquid between vessels, and also to provide for de-aeration of a sample confined in a vessel without loss of volatile components in the sample by fitting a septum in the vessel at liquid surface.

DESCRIPTION OF THE INVENTION

Figure 1:
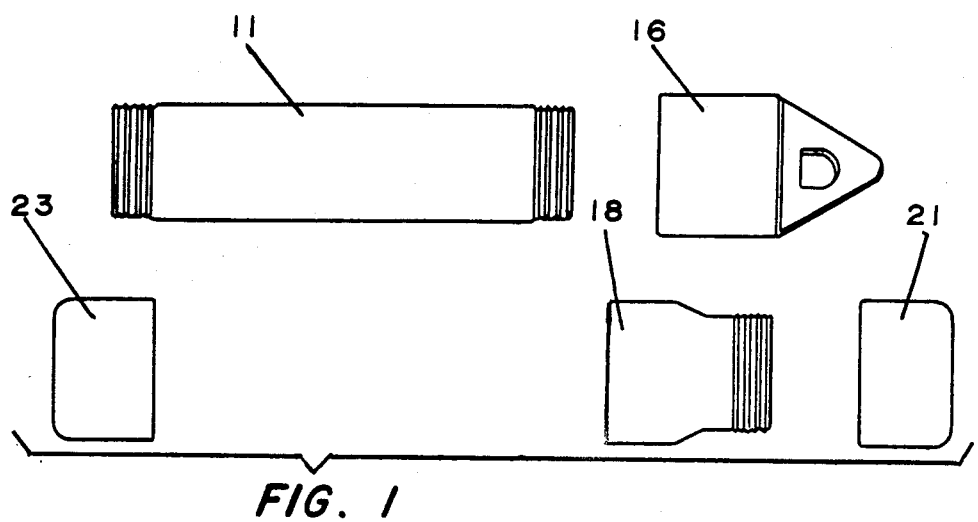
FIG. 1 is an elevation view of an embodiment of this invention consisting of components of a liquid sampling device shown in disassembled array.
Figure 2:
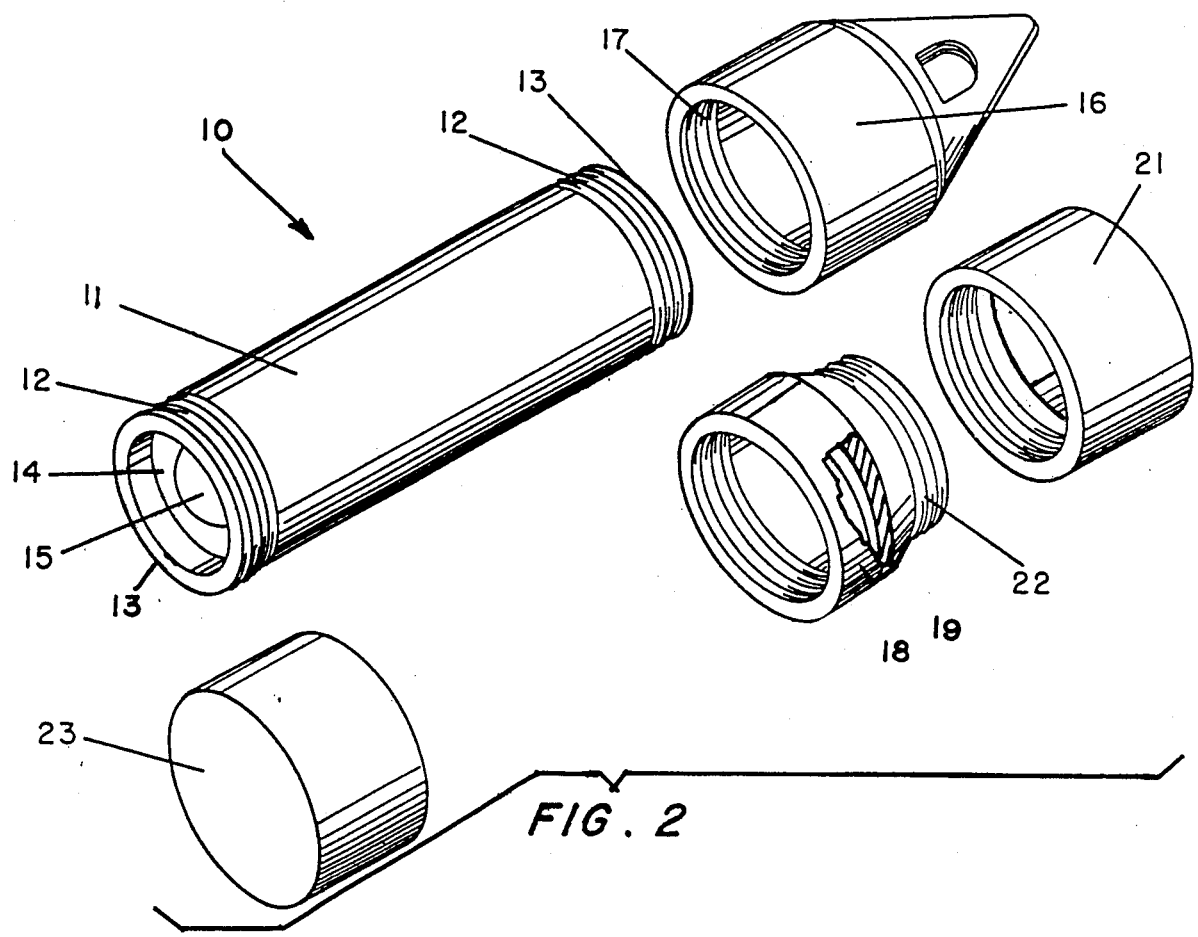
FIG. 2 is a perspective view of the embodiment of FIG. 1 consisting of components utilized for transport and storage functional employment of the device shown in disassembled array.

Referring to FIGS. 1 and 2, liquid sampler 10, shown disassembled in FIG. 1, comprises tubular body member 11 configured with external threads 12 on lower extremity 13 of member 11 and with similar threads 12' on upper extremity 13' of the member. Lower extremity of member 11 is provided with annular valve seat 14 and check valve 15 which latter component may either be of spherical configuration as shown or comprise a hinged flap or other conventional means. Bail top member 16 is shown comprising internal threads 17 which can be operably engaged with threads 12' on upper extremity 13' of body 11. Bail member 16 is preferably vented to enable air to escape from body member 11 when a liquid sample is filling the body. The bail configuration of member 16 allows a hook to be easily attached for lowering the device into a well, barrel or other body of liquid which is to be sampled. Upon lifting sampler 10 from immersion in a body of liquid, check valve 15 closes and prevents loss of contents through the bottom of the device while bail member 16 is unscrewed from body 11 carefully to avoid spilling of the contents of the sampler and is replaced, preferably, by septum fitting 18 screwed tightly onto threads 12' so as to place septum diaphram 19 in interfacing relationship with liquid contained in body member 11. An upward extending convexity for the meniscus on the liquid in body member 11 may be assumed so that a gaseous cavity does not exist below the septum diaphragm when fitting 18 is applied. Top closure fitting 21 may then be applied to threads 22 on the upper extremity of fitting 18, or if fitting 18 is eliminated, fitting 21 may be operably applied to threads 12' on body member 11 to seal the top of body member 11. An identical bottom closure member 23 is applied to threads 12 on body member 11 to seal the bottom of the sampler. So equipped, with top and bottom of body member 11 sealed and preferably with septum fitting 18 in place on body member 11, the vessel may be transported and stored in upright position until opened in a laboratory for analysis without deterioration resulting from aeration, cross-contamination or loss of volatile ingredients.

In FIG. 2, septum fitting 18 is shown in partial cross-section cutaway view to illustrate septum membrane 19 stretched across and sealed to the wall of the bore of fitting 18. An appropriate material for use, for example, is marketed under the trade name "Tuf-Bond Septa Discs".

A septum is an osmotic membrane which for use herein enables small gas molecules such as those of air to penetrate the membrane barrier and escape from dissolved or entrapped state in a liquid body without enabling larger molecules such as those of organic materials to pass even though the latter may be in vapor state. The selection of an appropriate membrane for a given liquid sample is within the ability of a person knowledgable in laboratory practice and sampling arts.

Variations in the apparatus of the invention can be made without departing from the inventive concept, for example, a septum diaphragm may be provided which can be placed directly on the top of the sample container body and a single cover member configured with an interior shoulder which contacts the diaphragm may be furnished and secured to the container body in substitution for the two piece septum fitting and end closure cap. Also, it is possible to provide bayonet type securing means instead of screw threads on the apparatus components or latches and gasket or O-rings seals between members to provide a sealed construction or to eliminate the need for handle bail if an attached line is anchored to a fitting stud or latch. The provision of such substitutes will be apparent to an artisan.

I claim:

1. Apparatus for obtaining a sample from a body of liquid comprising
   a. an elongated annular body member configured with externally threaded end extremity portions,
   b. a check valve disposed within said body member at the lower extremity thereof, said check valve being constructed to admit liquid into said body member by upward flow thereinto and to prevent liquid flow out of said body member by downward flow, said body member having a vented upper end extremity,
   c. a bail fitting for being secured to the upper extremity of said body member, said bail fitting being configured with an internally threaded lower extremity portion for being operably engaged with threaded extremity upper portion of said body member, and being further configured with an opening in the upper portion thereof for receiving therethrough a hook or clevis attached to a lifting line, d. a septum fitting for being secured to the upper extremity of said body member in substitution for said bail fitting after said latter fitting is removed, said septum fitting being configured with an internally threaded lower extremity portion for being operably engaged with the uppermost of said externally threaded end extremity portions of said body member and being further configured with an externally threaded upper extremity portion of character similar to said uppermost of said externally threaded end extremity portions of said body member, said septum fitting being further provided with a septum member disposed as a diaphragm sealed across a bore in said septum fitting to interface with the upper end extremity of said body member when said body member and said septum fitting are operably and tightly engaged in threaded connection, and with a liquid sample when said body member is filled with such sample, e. a pair of threaded caps one for being operably engaged with the lowermost of said externally threaded end extremity portions of said body member and another for being operably engaged with said septum fitting externally threaded upper extremity portion.

2. Apparatus for obtaining a sample from a body of liquid comprising a. a sample container body member configured with a check valve disposed at the lower extremity thereof for preventing liquid from draining from said body member and for enabling a sample of liquid in which said container body is immersed to enter into said container body, and further configured with means for sealably securing means covering at least one end of said container body member, b. a septum for being placed interfacing the upper end extremity of said container body member wherein said septum is an osmotic membrane, c. means for maintaining said septum in interfacing disposition with the upper end extremity of said body member wherein such means is configured for being operably attached to said container body member.

3. The apparatus of claim 2 wherein said means for maintaining said septum is configured to provide a closure for the upper end of said container body member.

4. The apparatus of claim 2 further comprising a bail member for use in lowering and lifting such apparatus.

5. The method of obtaining a sample of contents of a body of liquid and preserving such sample from deterioration resulting from aeration, contamination, or loss of volatile components comprising the steps of providing a container for confining a sample of liquid, immersing said container in the body of liquid to be sampled, removing said container when filled from said body of liquid, applying to the top of said container a septum, securing a cap on said container to maintain said septum in interfacing disposition with liquid in said container and to provide a volume above said septum into which dissolved and entrapped gaseous components in said sample can escape, thereby to preserve said sample against loss of quality prior to analysis.

* * * * *